(12) United States Patent
Barnes et al.

(10) Patent No.: US 9,827,448 B2
(45) Date of Patent: Nov. 28, 2017

(54) HYBRID ULTRASOUND AND MAGNETIC RESONANCE IMAGING DEVICE

(71) Applicants: Stephen R Barnes, Bellevue, WA (US); Patrick Gross, Ismaning (DE); Jerry D. Hopple, Seabeck, WA (US)

(72) Inventors: Stephen R Barnes, Bellevue, WA (US); Patrick Gross, Ismaning (DE); Jerry D. Hopple, Seabeck, WA (US)

(73) Assignee: Siemens Aktiengesellschaft, München (DE)

( * ) Notice: Subject to any disclaimer, the term of this patent is extended or adjusted under 35 U.S.C. 154(b) by 236 days.

(21) Appl. No.: 14/664,824

(22) Filed: Mar. 21, 2015

(65) Prior Publication Data

US 2015/0265857 A1    Sep. 24, 2015

Related U.S. Application Data

(60) Provisional application No. 61/968,956, filed on Mar. 21, 2014.

(51) Int. Cl.
| | |
|---|---|
| *A61B 5/055* | (2006.01) |
| *A61N 7/02* | (2006.01) |
| *G01R 33/48* | (2006.01) |
| *A61B 8/00* | (2006.01) |
| *A61B 8/08* | (2006.01) |
| *A61B 90/00* | (2016.01) |

(52) U.S. Cl.
CPC ............. *A61N 7/02* (2013.01); *A61B 5/055* (2013.01); *A61B 8/4416* (2013.01); *G01R 33/4814* (2013.01); *A61B 8/5246* (2013.01); *A61B 2090/374* (2016.02)

(58) Field of Classification Search
CPC ........... A61B 8/483; A61B 8/00; A61B 5/055; A61B 2018/00023; A61B 2019/5236; A61B 2090/374; A61N 7/00; A61N 2007/0078; A61N 2007/0086; A61N 2007/0091; A61N 7/02; G01R 33/4814; H04R 17/00; H04R 1/40
See application file for complete search history.

(56) References Cited

U.S. PATENT DOCUMENTS 4,782,298 A * 11/1988 Arakawa ............ G01R 33/3657
                                                   324/318
5,787,889 A *  8/1998 Edwards ............. G01S 15/8993
                                                   128/916

(Continued)

*Primary Examiner* — Vani Gupta
(74) *Attorney, Agent, or Firm* — Lempia Summerfield Katz LLC

(57) ABSTRACT

In order to position and simultaneously operate both a magnetic resonance (MR) coil and an ultrasound transducer adjacent to a target volume while minimizing interference between the MR coil and the ultrasound transducer, hybrid ultrasound and magnetic resonance imaging (MRI) devices are provided. One of the hybrid ultrasound and MRI devices includes a transducer array, a communications interface connected with the transducer array, and a housing that electromagnetically shields and encloses the transducer array and the communications interface. An electrically conducting side of the housing receives a radio frequency (RF) signal from an MRI system and transmits the RF signal to an electrically conducting side of a housing of another of the hybrid ultrasound and MRI devices.

12 Claims, 5 Drawing Sheets

(56) References Cited

U.S. PATENT DOCUMENTS

| | | | |
|---|---|---|---|
| 2004/0015079 A1* | 1/2004 | Berger | G01S 7/52025 600/437 |
| 2004/0073118 A1* | 4/2004 | Peszynski | A61B 8/12 600/459 |
| 2004/0267111 A1* | 12/2004 | Feinberg | A61B 8/08 600/411 |
| 2005/0131298 A1* | 6/2005 | Cai | G01S 15/8925 600/447 |
| 2005/0148878 A1* | 7/2005 | Phelps | A61B 8/546 600/459 |
| 2007/0167705 A1* | 7/2007 | Chiang | A61B 5/6805 600/407 |
| 2009/0016163 A1* | 1/2009 | Freeman | G01S 7/5208 367/103 |
| 2011/0210731 A1* | 9/2011 | Walsh | A61B 5/055 324/307 |
| 2013/0023418 A1* | 1/2013 | Ackermann | F25B 9/10 505/162 |

* cited by examiner

HYBRID ULTRASOUND AND MAGNETIC RESONANCE IMAGING DEVICE

This application claims the benefit of U.S. Provisional Application No. 61/968,956, filed on Mar. 21, 2014.

FIELD

The present embodiments relate to a hybrid ultrasound and magnetic resonance imaging (MRI) device used to image or treat an object with ultrasound radiation and image the object with MR.

BACKGROUND

For image guided procedures using, for example, ultrasound and magnetic resonance imaging (MRI) (e.g., magnetic resonance (MR) guided high-intensity focused ultrasound (HIFU)), an MR coil of an MRI system and a transducer of an ultrasound device are in direct competition. For example, the MR coil and the ultrasound transducer are in direct competition spatially. For the MR coil, a solid angle with respect to a target volume covered by the MR coil at least partially defines a signal-to-noise (SNR) ratio of the MRI system. For the HIFU transducer, a solid angle used by the transducer defines how much power may be applied and also has an impact on the focus shape and which areas may be reached. For a diagnostic ultrasound transducer, the solid angle has an impact on the resolution and imaging coverage.

The MR coil and the ultrasound transducer are also in direct competition as a result of electro-magnetic coupling between the MR coil and the ultrasound transducer. The ultrasound transducer includes a number of conducting structures such as, for example, a ground plane, shielding, and cables. The MR coil may couple to these conducting structures, thus resulting in detuning and additional coil losses. The electrical signals from the ultrasound transducer may also couple to the MR coil, thus interfering with the sensitive MR signal.

In the prior art, the direct competition between the MR coil and the ultrasound transducer is addressed, for example, by positioning the MR coil around or behind the ultrasound transducer. For example, a large loop MR coil may be used, and an opening formed by the loop MRI coil serves as an acoustic window. This has disadvantages that the MR coil is electrically large and difficult to realize at higher field strength. Also, the large size of the MR coil places the inductive loop far from the signal emitting spins of the target volume. As another example, the MR coil is positioned behind the ultrasound transducer. This too places the MR coil further away from the target volume. Also, the MR coil may couple to the ultrasound transducer, thus reducing the quality factor of the MR coil and therefore the attainable SNR.

The direct competition between the MR coil and the ultrasound transducer may also be addressed, for example, by designing the MR coil and/or the ultrasound transducer such that coupling between the MR coil and the US transducer is minimized. For example, floating grounds and baluns, and smaller individual ultrasound transducers may be provided.

SUMMARY

In order to position and simultaneously operate both a magnetic resonance (MR) coil and an ultrasound transducer adjacent to a target volume while minimizing interference between the MR coil and the ultrasound transducer, hybrid ultrasound and magnetic resonance imaging (MRI) devices are provided. One of the hybrid ultrasound and MRI devices includes a transducer array, a communications interface connected with the transducer array, and a housing that electromagnetically shields and encloses the transducer array and the communications interface. An electrically conducting side of the housing receives a radio frequency (RF) signal from an MRI system and transmits the RF signal to an electrically conducting side of a housing of another of the hybrid ultrasound and MRI devices.

In a first aspect, a hybrid ultrasound and MRI device is provided. The hybrid ultrasound and MRI device includes a transducer array including a multi-dimensional array of elements. The hybrid ultrasound and MRI device also includes a communications interface connected with the transducer array. The hybrid ultrasound and MRI device includes a housing operable to electromagnetically shield and enclose the transducer array and the communications interface. The housing includes an electrically conducting side. The electrically conducting side is configured to receive an RF signal from an MRI system and transmit the RF signal to an electrically conducting side of a housing of another hybrid ultrasound and MRI imaging device.

In a second aspect, an RF loop antenna for a magnetic resonance imaging (MRI) system is provided. The RF loop antenna includes housings each including an electrically conducting side. The RF loop antenna also includes a plurality of transducer arrays. Each transducer array of the plurality of transducer arrays is electromagnetically shielded and enclosed by a corresponding one of the housings and includes a multi-dimensional array of elements. The RF loop antenna also includes communications interfaces that are each electromagnetically shielded and enclosed by the corresponding one of the housings. Each of the communications interfaces is in communication with a corresponding transducer array of the plurality of transducer arrays. The RF loop antenna includes tuning capacitors. Each of the tuning capacitors electrically connects the electrically conducting sides of two of the housings, respectively.

In a third aspect, a method for treating and imaging an object is provided. The method includes positioning a plurality of hybrid ultrasound and MRI devices on or adjacent to an object. Each hybrid ultrasound and MRI device of the plurality of hybrid ultrasound and MRI devices includes a transducer array and a housing operable to electromagnetically shield and enclose the transducer array. Each of the housings includes an electrically conducting side. The plurality of hybrid ultrasound and MRI devices are electrically connected to one another via the electrically conducting sides to form an RF loop antenna. RF signals are transmitted to the object, or signals are received from the object via the RF loop antennas. The object is irradiated using the transducer arrays of the plurality of hybrid ultrasound and MRI devices.

DETAILED DESCRIPTION

Figure 1:
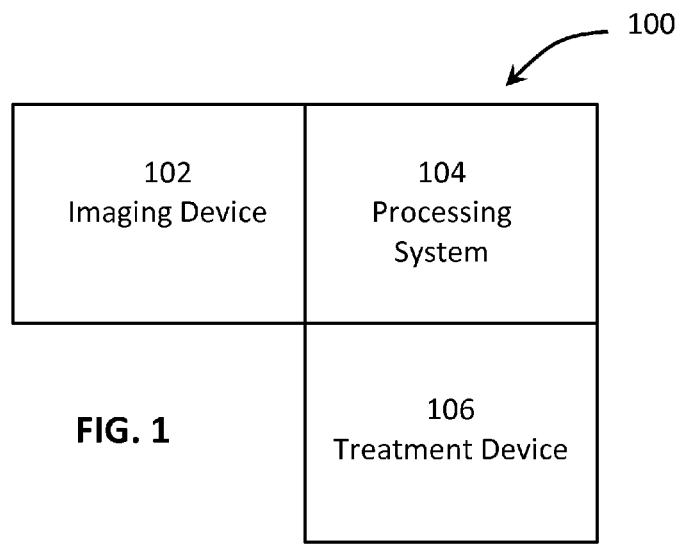
FIG. 1 shows one embodiment of an image-guided therapy system.

In high intensity therapeutic ultrasound (HITU), there is a direct conflict between using available patient surface area for HITU or ultrasound imaging transducers or for magnetic resonance (MR) transmit and/or receive coils. An ultrasound transducer requires coupling to the patient through an acoustic window. The area visible to the ultrasound transducer is defined by the acoustic window. Further, when high powers are delivered to a region, the area available may be critical, as the lower power seen by tissue is divided by an area of a solid angle. From an MR perspective, the Maxwell equations make it attractive to have the MR coils close to the tissue to be imaged. The sensitivity of the MR coils decreases substantially with the distance.

Due to the direct conflict between the ultrasound transducers and the MR transmit and/or receive coils, an ultrasound device and an MR device are combined into a hybrid device (e.g., a combined device). Magnetic resonance (MR) coils may be formed by shield cans (e.g., shielding containers) or other structures used to contain electronics for operating the ultrasound device. For example, a shield of a fully RF shielded ultrasound device is used as part of the conducting structures of an MR coil. A loop of a square loop coil may be constructed from four shielded ultrasound devices, for example. The ultrasound devices may be configured as substantially rectangular (e.g., flat) boxes, and the rectangles may be arranged to form a square with edges coupled by capacitors. Combinations of such squares may be provided to form an MR coil array.

The conflict between the ultrasound transducers and the MR transmit and/or receive coils is thus resolved with the MR coil occupying the same space as the ultrasound device. Through arrangements of alternating current (AC) coupling and circuit isolation methods, both the MR coils and the ultrasound device may be operated at the same time in the same space. This is enabled, in part, by the difference in operating frequency between the MR coils (e.g., 64 or 128 MHz) and the ultrasound device (e.g., 1-5 MHz).

To allow the modules to function as both active receiver coils for MR, for example, and functional transmit/receive transducers for ultrasound, the traditional ultrasound transducer design may not be used. The traditional US transducer design includes hundreds or thousands of coaxial wires, and each of the coaxial wires includes a grounded shield that is decoupled from the other grounded shields using, for example, a balun to allow the shielded modules to also be active at the MR frequencies.

Dense circuitry used to drive and receive on large arrays used for phased ultrasound therapy and imaging ultrasound transducers may be contained within small discrete sections with only DC power (e.g., small wire count and easier to decouple compared to the traditional US transducer design) and fiber or similar input/output connections. The small discrete sections may be located in the shield can, at a transducer active face. This enables the use of the shielding containers for the MR coils.

An ultrasound transducer may be completely shielded with an electrically conductive (e.g., copper) surface at a front surface of the ultrasound transducer. In order to remove the effects of, for example, power losses and geometric competition, the electrically conductive surface may form at least a portion of the electrically conductive tracks (e.g., copper tracks) of the MR coil. In other words, conductive structures of the ultrasound transducers are used as conductive structures of the MRI coil.

Available application specific integrated circuits (ASICs) enable ultrasound transducers that are self contained and may be enclosed in loop like structures without the need for thousands of wires in and out of the ultrasound device. The MR coil may use structures of the ultrasound device as receive and/or transmit coil(s) for an MR machine. Coupling electronics are configured such that the enclosures of the ultrasound device (e.g., the shielding containers) may both be an effective ground return at the ultrasound frequencies and an active antenna at the MR frequencies.

FIG. 1 shows one embodiment of an image-guided therapy system 100 (e.g., therapy system). The image-guided therapy system 100 may be used in the system and method described below. The therapy system 100 may include one or more imaging devices 102 (e.g., an imaging device), one or more image processing systems 104 (e.g., an image processing system), and one or more treatment devices 106 (e.g., a treatment device). A dataset representing a two-dimensional (2D) or a three-dimensional (3D) (e.g., volumetric) region may be acquired using the imaging device 102 and the image processing system 104 (e.g., an imaging system). The 2D dataset or the 3D dataset may be obtained contemporaneously with the planning and/or execution of a medical treatment procedure or at an earlier time. Additional, different or fewer components may be provided.

In one embodiment, the imaging system 102, 104 is, for example, an MRI system. The imaging system 102, 104 may be used to create a patient model that may be used in the planning of the medical treatment procedure (e.g., HIFU therapy). For example, the image processing system 104 is a workstation for treatment planning for HIFU therapy in a patient. In other embodiments, the imaging system 102, 104 may include, for example, a medical workstation, a computed tomography (CT) system, an ultrasound system, a positron emission tomography (PET) system, an angiography system, a fluoroscopy, an x-ray system, any other now known or later developed imaging system, or a combination thereof. The workstation 104 receives data representing or images of the patient (e.g., including at least part of the liver of the patient) generated by the imaging device 102.

The treatment device 106 may be image guided by the imaging system 102, 104. The treatment device 106 may be any number of treatment devices including, for example, a HIFU transducer. The HIFU transducer 106 may use HIFU to transmit acoustic energy into tissue (e.g., of the liver). The acoustic energy heats and/or destroys the tissue through ablation. The HIFU transducer 106 may be image guided to allow treatment planning and targeting before applying the acoustic energy. In one embodiment, the HIFU transducer 106 is MRI-guided (e.g., MRgHIFU). The position, transmission, or other operation of the HIFU transducer 106 may be controlled by the image processing system 104 or another controller (e.g., a beamformer system). The therapy system 100 may include more or fewer components.

Figure 2:
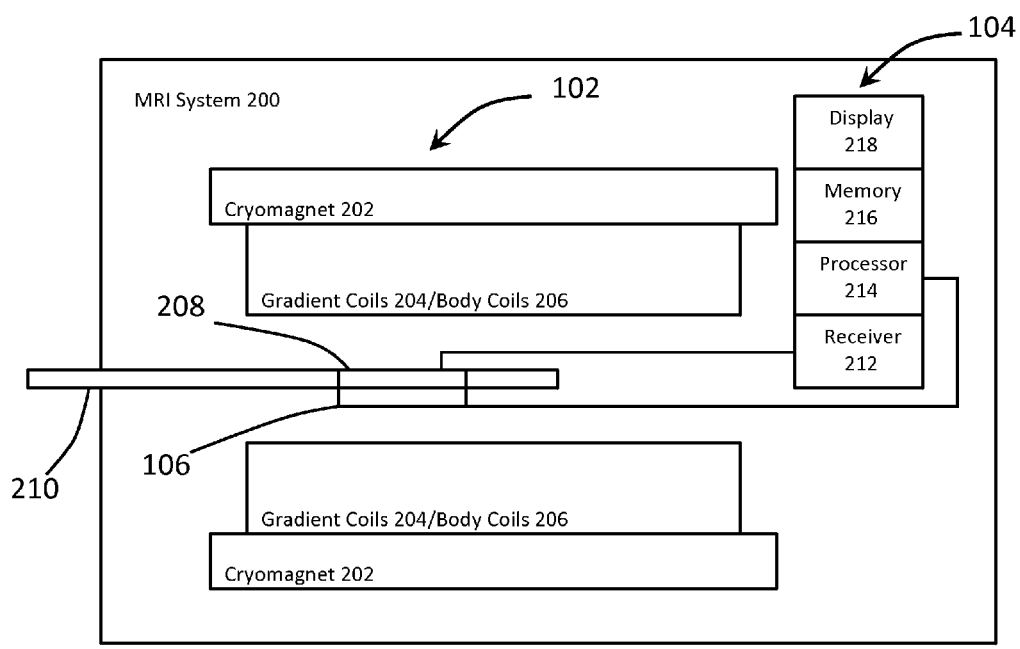
FIG. 2 shows one embodiment of a magnetic resonance imaging system.

FIG. 2 shows one embodiment of an MRI system 200. The MRI system 200 includes an MRI device 102 and the image processing system 104. The MRI device 102 includes a cryomagnet 202, gradient coils 204, a whole body coil 206 (e.g., body coils), a local coil 208, and a patient bed 210. The image processing system 104 may include an MR receiver 212, a processor 214, a memory 216, and a display 218. Additional, different, or fewer components may be provided.

For example, an additional local coil or an additional surface coil may be provided for MR imaging. Additionally, a user input device (e.g., a keyboard and/or a mouse) may be provided for user control. As another example, the whole body coil 206 is not provided.

Other parts of the MRI system 200 are provided within a same housing, within a same room (e.g., within a radio frequency cabin), within a same facility, or connected remotely. The other parts of the MRI system 200 may include cooling systems, pulse generation systems, additional image processing systems, and user interface systems. Any now known or later developed MR imaging system may be used. The location of the different components of the MRI system 200 is within and/or outside the RF cabin, such as the imaging processing, tomography, power generation, and user interface components being outside the RF cabin. Power cables, cooling lines, and communication cables connect the pulse generation, magnet control, and detection systems within the RF cabin with the components outside the RF cabin through a filter plate.

In one embodiment, the processor 214 and the memory 216 are part of the MR receiver 212. Alternatively, the processor 214 and the memory 216 are part of an archival and/or image processing system, such as associated with a medical records database workstation or server. In yet other embodiments, the processor 214 and the memory 216 are a personal computer such as a desktop or a laptop, a workstation, a server, a network, or combinations thereof. The processor 214 and the memory 216 may be provided without other components for implementing the method.

The cryomagnet 202, the gradient coils 204, and the body coils 206 are in the RF cabin, such as a room isolated by a Faraday cage. A tubular or laterally open examination subject bore encloses a field of view. A more open arrangement may be provided. The patient bed 210 (e.g., a patient gurney or table) supports an examination subject such as, for example, a patient with a local coil arrangement including the local coil 208. The patient bed 210 may be moved into the examination subject bore in order to generate images of the patient. In the embodiment shown in FIG. 2, the local coil 208 is located in the patient bed 210 (e.g., below a patient). In other embodiments, the local coil 208 may be located between the patient bed 210 and the patient, on a side of the patient, and/or above the patient, for example. Received signals may be transmitted by the local coil 208 to the MR receiver 212 via, for example, coaxial cable or radio link (e.g., via antennas) for imaging.

In order to examine the patient, different magnetic fields are temporally and spatially coordinated with one another for application to the patient. The cryomagnet 202 generates a strong static main magnetic field $B_0$ in the range of, for example, 0.2 Tesla to 3 Tesla or more. The main magnetic field $B_0$ is approximately homogenous in the field of view.

The nuclear spins of atomic nuclei of the patient are excited via magnetic radio-frequency excitation pulses that are transmitted via a radio-frequency antenna, shown in FIG. 2 in simplified form as a whole body coil 206 and/or possibly a local coil arrangement (e.g., the local coil 208 or local coils). Radio-frequency excitation pulses are generated, for example, by a pulse generation unit controlled by a pulse sequence control unit. After being amplified using a radio-frequency amplifier, the radio-frequency excitation pulses are routed to the body coils 206 and/or the local coils 208. Each of the body coils 206 is a single-part or includes multiple coils. The signals are at a given frequency band. For example, the MR frequency may be about 64 or 128 MHz. In one embodiment, "about" may include frequencies+/−500 kHz the 64 or 128 MHz MR frequency. Different center frequencies and/or bandwidths may be used.

The gradient coils 204 radiate magnetic gradient fields in the course of a measurement in order to produce selective layer excitation and for spatial encoding of the measurement signal. The gradient coils 204 are controlled by a gradient control unit that, like the pulse generation unit, is connected to the pulse sequence control unit. The gradient control unit, the pulse generation unit, and/or the pulse sequence control unit are represented, at least in part, by the processor 214 or another controller.

Signals emitted as a result of the excited nuclear spins are received by the local coil 208. In some MR tomography procedures, images having a high signal-to-noise ratio (SNR) may be formed using the local coil arrangement (e.g., loops, local coils). The local coil arrangement (e.g., antenna systems) is disposed in the immediate vicinity of the examination subject on (anterior) or under (posterior) or in the patient. The received signals are amplified by associated radio-frequency preamplifiers, transmitted in analog or digitized form, and processed further and digitized by the MR receiver 212. The digitized data is stored in the memory 216 as complex numeric values in a k-space matrix. An associated MR image of the examination subject may be reconstructed using a one-dimensional or a multidimensional Fourier transform (FT) from the k-space matrix populated with values. Reconstructed MR images of the examination subject may be stored in the memory 216 and/or displayed on the display 218.

The local coil 208 connects with the MR receiver 212. The connection is wired (e.g., using a coaxial cable) or wireless. The connection is for data from the local coil 208 to be transmitted to and received by the MR receiver 212. The data is K-space data. In response to an MR pulse, the local coil 208 receives signals and transmits the K-space data to the MR receiver 212. Any pulse sequence, such as a simple pulse sequence acquiring projections along three spatial axes, may be used. Any spatial resolution may be provided (e.g., a spatial resolution of 3 mm).

The MR receiver 212 includes the processor 214 or another processor (e.g., a digital signal processor, a field programmable gate array, or an application specific circuit for applying an inverse Fourier transform) for reconstructing the K-space data. The MR receiver 212 is configured by hardware or software to calculate X, Y, and Z projection data from the K-space data.

In the course of an MR measurement, the excited nuclei induce a voltage in the local coil 208. The induced voltage is amplified by a low-noise preamplifier (e.g., LNA, preamp) and forwarded to the MR receiver 212. Other transforms for reconstructing spatial data from the K-space data may be used.

The processor 214 is a general processor, a central processing unit, a control processor, a graphics processor, a digital signal processor, a three-dimensional rendering processor, an image processor, an application-specific integrated circuit, a field-programmable gate array, a digital circuit, an analog circuit, combinations thereof, or other now known or later developed device for image processing. The processor is a single device or multiple devices operating in serial, parallel, or separately. The processor 214 may be a main processor of a computer, such as a laptop or desktop computer, or may be a processor for handling some tasks in a larger system, such as being part of the MR receiver 212 or the imaging system 104. The processor 214 is configured by instructions, design, hardware, and/or software to perform the acts discussed herein, such as guiding the positioning of a masking material for rib protection from acoustic energy emitted by an ultrasound transducer.

The memory 216 is a computer readable storage media. The computer readable storage media may include various types of volatile and non-volatile storage media, including but not limited to random access memory, read-only memory, programmable read-only memory, electrically programmable read-only memory, electrically erasable read-only memory, flash memory, magnetic tape or disk, optical media and the like. The memory 216 may be a single device or a combination of devices. The memory 216 may be adjacent to, part of, networked with and/or remote from the processor 214.

The display 218 is a monitor, a CRT, an LCD, a plasma screen, a flat panel, a projector or other now known or later developed display device. The display 208 is operable to generate images for a two-dimensional view or a rendered three-dimensional representation. For example, a two-dimensional image representing a three-dimensional volume through rendering is displayed.

FIG. 2 also shows the treatment device 106 disposed below the patient table 210. The treatment device 106 may be disposed anywhere around the examination subject (e.g., above and/or on a side of the examination subject).

The treatment device 106 may include, for example, an HIFU transducer and a beamformer or transmitter system. The treatment device 106 and the local coil 208 may form a hybrid ultrasound-MR device (shown in FIG. 4). The treatment device 106 includes a surface at a front of the HIFU transducer that shields the HIFU transducer. The shielding surface is electrically conductive (e.g., made of copper), and the local coil 208 may be at least partially formed from the electrically conductive shielding surface. The HIFU transducer may focus ultrasound waves into a small focal zone at a given depth. In other embodiments, the HIFU transducer may be a multidimensional transducer array, a one-dimensional transducer array, or any other now known or later discovered HIFU transducer.

The beamformer system includes, for example, a transmit beamformer with multiple channels for electrically forming a beam from an array of elements. The beamformer system may also include one or more lenses (e.g., a polystyrene lens) for focusing the ultrasound waves into the small focal zone, filters, position sensors, combinations thereof and/or other now known or later developed components for HIFU. The treatment device 106 (e.g., the HIFU transducer and the beamformer) may be controlled by the processor 214 and/or another processor.

Using the treatment device 106, acoustic energy is transmitted into tissue (e.g., the liver) of the examination subject. In one embodiment, the treatment device 106 may be used for tissue ablation (e.g., using the HIFU transducer) in tumor treatments (e.g., of the liver). In other embodiments, the treatment device 106 may be used for hyperthermia treatments, causing cavitation, clot breaking, or for the activation of or enhanced delivery of drugs.

For ablation of a tumor on or in the examination subject, for example, the ultrasound waves emitted by the HIFU transducer are focused at a natural focus point (e.g., a focal point, a focal region) of the transducer. The HIFU transducer may be positioned relative to the examination subject, or the examination subject may be positioned relative to the HIFU transducer, such that the natural focus point of the HIFU transducer is located at the tumor to be ablated. Pre-ablation MR images may be used to locate the tumor and position the HIFU transducer. MR images may also be generated and used to track the tumor and the position of the HIFU transducer during the ablation procedure.

Figure 3:
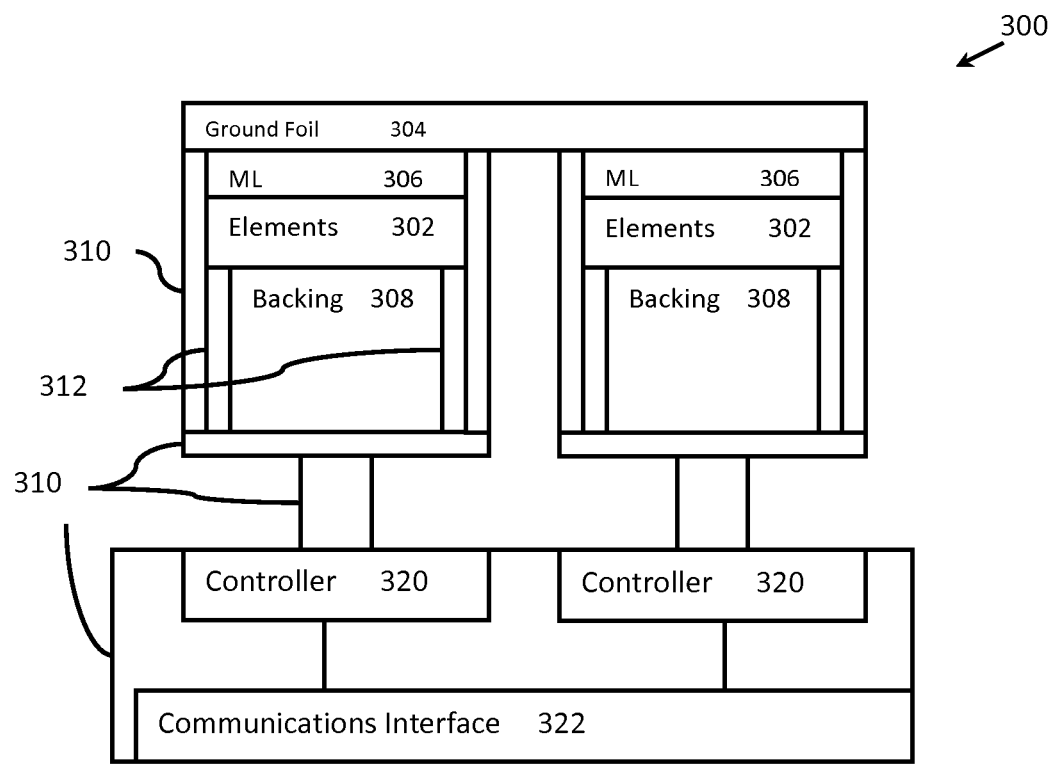
FIG. 3 shows one embodiment of a therapeutic ultrasound device.

FIG. 3 shows one embodiment of a compact, integrated therapeutic ultrasound device 300 for use, at least in part, with the MRI system 200. The therapeutic ultrasound device 300 may form part of the hybrid ultrasound-MR device. The ultrasound device 300 includes elements 302 of a transducer array, a ground foil 304 for the elements 302, an acoustic matching layer 306, acoustically absorbing backing 308, a housing 310, a transmit beamformer 312, controllers 320, and a communications interface 322. Additional, different, or fewer components may be provided. For example, fluid channels and a membrane are provided. As another example, the communications interface 322, the controller 320, and/or the transmit beamformer 312 are combined together, such as on a semiconductor.

The elements 302, the backing 308, the matching layer 306, and/or the ground foil 304 may be considered part of the transducer for converting between electrical and acoustical energy. The transducer may include additional components, such as a signal electrode for each element 302.

The housing 310 limits or prevents electromagnetic interference. The housing 310 electromagnetically shields and encloses the transducer array, the transmit beamformer 312 and the communications interface 322. The transducer and drive electronics are a fully contained unit, with computational resources or precomputed parameter tables and the drive amplifiers all inside an EMI shielded enclosure of the housing 310. System transmitters, the beamformer 312, the communications interface 322, and the high element count transducer array are located in close proximity to the patient and each other.

For therapeutic ultrasound, the housing 310 does not enclose a receive beamformer. A receive beamformer is not provided as part of the therapeutic ultrasound device 300. Alternatively, a receive beamformer is provided, such as on a same application specific integrated circuit as the transmit beamformer 312 or on a separate component adjacent to the transmit beamformer 312.

The housing 310 has any shape. In the embodiment shown in FIG. 3, the housing 310 extends around the transducer and the transmit beamformer 312. The housing 310 includes a neck region connecting between the transducer and the controller 320. The controller 320 and the communications interface 322 are within the same housing 310. The housing 310 may include compartments or separation of components to limit electromagnetic interference. For example, the communications interface 322 is on a printed circuit board. The housing 310 surrounds the printed circuit board other than a gap for input and/or output wires, traces, or cables (e.g., flexible circuit input/output). Similarly, the controller 320 is in a separate chamber of the housing 310 other than a gap for input and/or output wires, traces, or cables, such as serial data and power for the transmit beamformer 312. Other housing arrangements may be provided, such as positioning the controller 320 and/or the communications interface 322 within a same box or chamber as the transmit beamformer 312, with the transducer in the same or different housing or chamber. Separate housings 310 may be provided for the different components.

In one embodiment, the housing 310 is a copper box or cube, at least for the transducer portion. The housing 310 may be made of any number of other electrically conducting materials such as, for example, brass. For example, the housing 310 includes four lateral sides with an open top and bottom for manufacture of the transducer. The top of the box is formed from the ground foil 304. The matching layer 306, the elements 302, the backing 308, and the transmit beamformer 312 are within this chamber or box of the housing 310.

The ground foil 304 is copper, aluminum or other conductive foil. An adhesive, such as silicone, epoxy, or solder, seals the ground foil 304 to the housing 310. The adhesive includes conductive particles, or the ground foil 304 is in contact with the conductive housing 310 for grounding.

For manufacture, the back of the box between the backing 308 and the controller 320 is a plate, such as a plate of copper or brass. After insertion or forming of the transducer in the housing 310, the back plate is connected with and sealed to the side walls of the housing 310. A gap may be provided in the back plate for flexible circuit material. The flexible circuit material is used for routing traces to electrically connect the transmit beamformer 312 to the controller 320.

The housing 310 is sealed such that fluids may not enter. For example, the use of adhesive silicone, epoxy, or solder may both hold parts of the housing 310 together and also provide a water tight seal. In alternative embodiments, a fluid tight seal is not used.

In one embodiment, a single housing 310 is used for a given transducer. In the embodiment shown in FIG. 3, a modular approach is used. The transducer, transmit beamformer 312, and controller 320 are provided in each module. Each module corresponds to a sub-array, such as a 40×40 arrangement of elements 302. To form the overall transducer, a plurality of modules is positioned adjacent to each other. Each module includes a separate housing 310. The transducer array is constructed of self-contained sub-arrays that include sub-arrays of elements 302 and transmit beamformers 312.

Any arrangement may be provided within a given module. In the embodiment shown in FIG. 3, the semiconductor chip or chips forming the transmit beamformer 312 are thermally bonded to the housing 310. On an opposite side of the chip from the housing 310, flexible circuit material connects input and output pads with the elements 302 and the controller 320. The ground foil 304 seals the transducer within the housing 310 of the module. While the elements 302 are shown extending to the housing 310, the elements 302 may have less lateral extent. Similarly, the transmit beamformer 312 may have less height, allowing the backing 308 to be positioned behind all of the elements 302 of the module. The elements 302 are positioned against the ground foil 304 for transduction. One or more acoustic matching layers 306 may be between the elements 302 and the ground foil 304. Alternatively, the matching layer 306 may be outside the module on the other side of the ground foil 304.

The modules are positioned in a flat plane to form a flat emitting face of the transducer. Alternatively, the modules are positioned to form a curved surface for focusing and/or conforming to the patient. The connection between the modules may be flexible. Alternatively, the connection is rigid, such as bonding the modules to the housing to a flat or curved upper plate of the housing 310 of the communications interface 322. Similarly, the elements 302 in each module are arranged over a flat or curved surface with or without an ability to flex relative to each other.

The housing 310, whether for a module, a group of modules, or the overall transducer and transmit beamformer 312, may be sized, shaped, or arranged to connect with the patient table 210 of the MRI system 200. In one embodiment, at least part of the outer housing of the hybrid ultrasound-MR device is formed by the module housing 310.

The hybrid ultrasound-MR device is positioned in an indention or hole in the table 38. The hybrid ultrasound-MR device may be raised relative to the table 210 to allow contact with the patient. Inflatable chambers and/or other robotic devices may be used to move the hybrid ultrasound-MR device into and out of contact with the patient lying on the patient table 210. In alternative embodiments, the hybrid ultrasound-MR device is part of a cuff or blanket to be worn by the patient or positioned on an arm or other device for setting the applicator hybrid ultrasound-MR device adjacent to the patient while in the bore of the MRI system 200. In yet other embodiments, the hybrid ultrasound-MR device is thin enough to lay on top of the table 210 without alteration of the table 210. For example, the hybrid ultrasound-MR device has a thickness similar to cushions on the table.

Whether formed as a single array or as a collection of sub-arrays, the transducer includes a plurality of elements 302. The transducer is a multi-dimensional array of piezoelectric or capacitive membrane elements. The elements are distributed along a rectangular, triangular or other grid pattern over two dimensions, such as N×M elements where both N and M are greater than 1.

For modules, the elements 302 of the array may include gaps. The gaps may be about one to ten elements wide. Since the elements 302 of the different modules are used as part of the same aperture for therapeutic transmission, the elements 302 from the different modules are part of the same transducer array.

Any number of elements 302 may be used. In one embodiment, there are at least 1,600 elements. An efficient, high power, high channel count high intensity ultrasound array system may have more than 1,500 elements for providing up to 3.3 KVA power for system and all support functions and may be capable of producing greater than 150 acoustic watts of applied acoustic energy. Using sixteen modules of 40×40 arrangements of elements 54 may allow for over 25,000 elements in one array. In one embodiment, sixteen modules of 1,152 elements each are arranged in a 2×8 arrangement for around 16,000 elements (e.g., see FIG. 5).

The transmit beamformer 312 is an application specific integrated circuit. Discrete components, processors, field programmable gate arrays, memories, digital-to-analog converters, or other devices may alternatively or additionally be used. For a given sub-array or for the entire array, one or more transmit beamformers 312 may be used. For example, two, three, or four separate chips are provided for a 40×40 or other sub-array. In one embodiment, each module has 12×36 elements with 32 transmitter chips (36 channels each) and 16 beamformer chips (72 channels each)). 228 channels or other numbers per chip may be used.

The transmit beamformer 312 includes a memory, delays, amplifiers, transistors, phase rotators, and/or other devices arranged in channels. Each channel generates a transmit waveform for a given element 302. The channels are associated with specific elements 302. Alternatively, a multiplexer allows channels to connect with different elements 302 at different times.

The transmit beamformer 312 causes the transducer array to form a therapeutic beam of acoustic energy. Any dose or power may be output. For example, acoustic power greater than 100 Watts continuous wave power is generated.

The controller 320 is a transmit beamformer controller. A processor, application specific integrated circuit, analog circuit, digital circuit, memory, combinations thereof, or other device may be used. The controller 320 receives high level commands through the communications interface 322 and processes the commands to configure the transmit beamformer 312. For example, a focal location is received. The controller 320 determines the delays and/or phase shifts for steering to the focal location. The delays and/or phase shifts may be loaded from memory or calculated. As another example, the frequency and/or amplitude is set by the controller 320. In another embodiment, the transmit beamformer 312 determines the delays and/or phase shifts so that the controller 320 controls the transmit beamformer 312 over fewer wires (e.g., single wire or high speed serial bus).

The controller 320 may configure the transmit beamformer 312 for response to a trigger input. The therapy may operate in conjunction with monitoring by the MR system 200. The controller 320 causes the transmit beamformer 312 to generate waveforms for therapy when triggered by the MRI system 200 or in synchronization with the MRI system 200. The scanning or imaging by the MRI system 200 may be interleaved with the therapy, so the triggering may be repeated.

By collocating drive amplifiers and the multi-dimensional array of elements 302, there is no bundle of coax cables. Instead, control signals are received by the controller 320. The controller 320 communicates over one or more traces or signal lines within the housing 310 to the adjacent (e.g., 0.1-10 cm away) transmit beamformer 312. Without the need to manage a large number of coax cables or other impedance controlled methods of interconnection, the array may be finely divided (e.g., hundreds or thousands of elements) to steer the beam without a need for robotic aiming or other supplemental mechanical motion control.

By positioning the transmit beamformer 312 adjacent to the elements 302, the electrical impedance mismatch associated with feet of coaxial cabling may be less. A mismatch may still occur due to the capacitance of the elements 302. The elements 302 are formed, in part, from spaced apart electrodes, such as a signal electrode spaced from the ground foil 304 by PZT.

The communications interface 322 is a circuit for transmitting and receiving high level controls from the processor 214 or another processor and to the controllers 320. In one embodiment, the communications interface 322 is an Ethernet interface. The communications interface 322 may route signals or data as addressed to the controllers 320. Alternatively, all data goes to all the controllers 320. The communications interface 322 connects with the transmit beamformers 312 through the controllers 320 for setting and causing therapeutic transmissions.

The communications interface 322 may include a connection to receive direct current power for the hybrid ultrasound-MR device. For example, a 100 volt DC connection is provided over a coaxial cable. 3-phase 10 KVA power may be provided. The power cable may include shielding and baluns to reduce electromagnetic interference. The communications interface 322 routes the power to the transmit beamformers 312. Voltage dividers, regulators, or other devices in the communications interface 322, controllers 320, or transmit beamformers 312 may condition the power for the digital signal processing.

The communications interface 322 communicates steering and other operation information received from, for example, the processor 214 of the MRI system 200 or another processor to the controllers 320. The steering information may indicate one or more locations for therapy. The waveforms to be applied to the elements 302 are not provided over the connection to the communications interface 322. Characteristics of the channel waveforms may be indicated, such as apodization, duration, frequency and/or aperture.

Using the transmit beamformer 312 allows for a minimal number of external electrical connections, such as only two external electrical connections, one for DC power and the other for a simple communication link to supply high level therapeutic power deposition information. The data bandwidth requirement for this level of information is minimal and may be implemented in a number of ways, such as with an MR compatible optical communication. By collocating computation resources, phase and power apodization calculations may be done locally, eliminating the need for a high speed, high bandwidth communication link to an external computational engine. System control may be located in the hybrid ultrasound-MR device, requiring only an external monitor and keyboard, or external interface for high level commands regarding the therapeutic ultrasound energy deposition.

Figure 4:
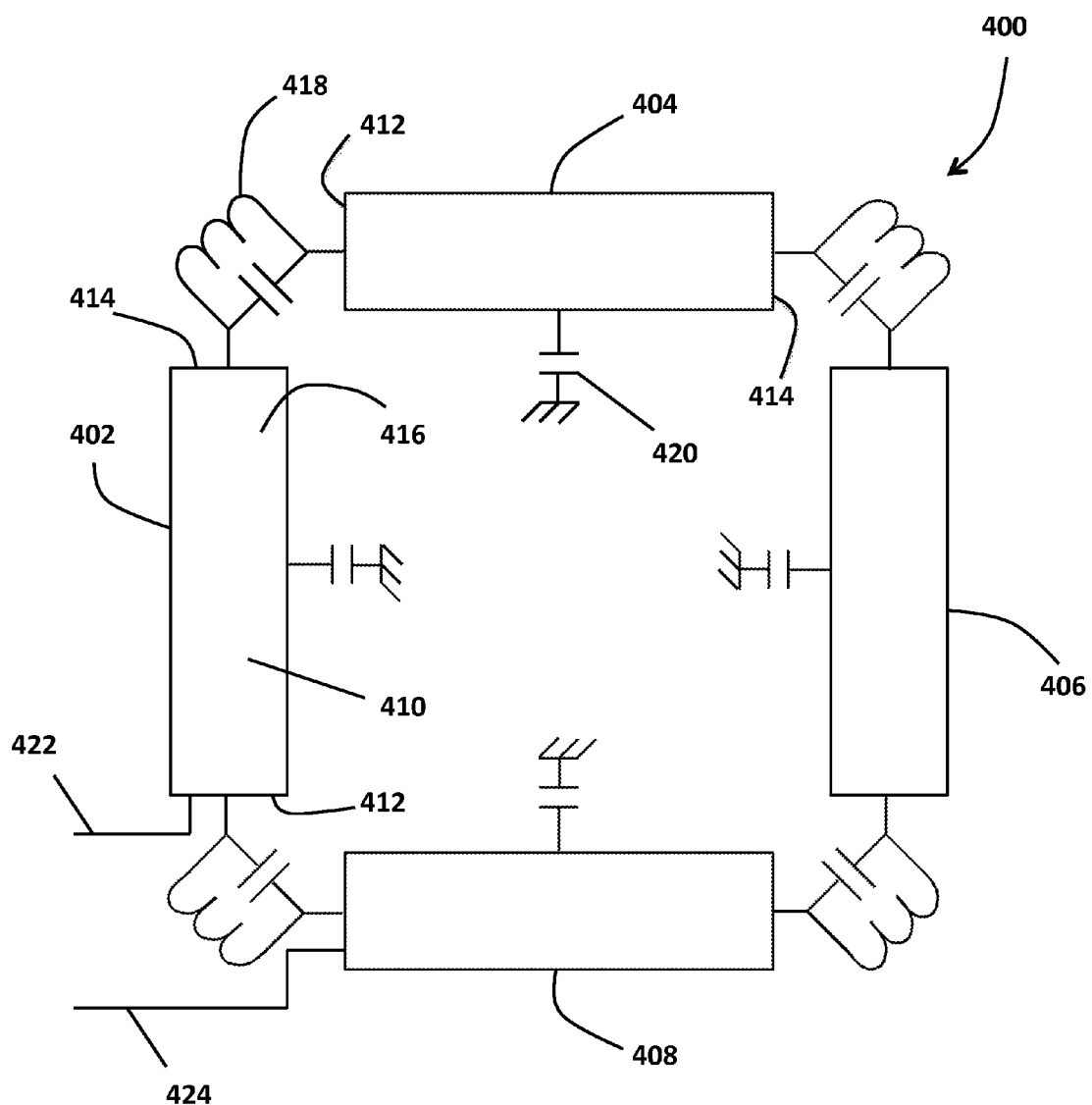
FIG. 4 shows one embodiment of a hybrid ultrasound-MR device.

FIG. 4 shows one embodiment of a hybrid ultrasound-MR device 400. The hybrid ultrasound-MR device may be used as both the treatment device 106 and the local coil 208 of the MRI system 200 of FIG. 2. The hybrid ultrasound-MR device 300 may also be used in another MRI system.

The hybrid ultrasound-MR device 400 shown in FIG. 4 includes four ultrasound modules 402, 404, 406, 408 (e.g., a first module 402, a second module 404, a third module 406, and a fourth module 408). Each of the modules 402, 404, 406, 408 corresponds to a sub-array, as described above with reference to FIG. 3. Each of the modules 402, 404, 406, 408 includes a housing 410. The local coil 208, for example, may be formed, at least partly, by the four module housings 410. The hybrid ultrasound-MR device 400 may include more or fewer modules and corresponding module housings 410 forming the local coil 208.

Housings 410 of the four modules 402, 404, 406, 408, for example, may be electrically connected to each other. Each of the four modules 402, 404, 406, 408 may be electrically connected to adjacent modules. For example, the housing 410 of the first module 402 may be electrically connected to the housing 410 of the second module 404 and the housing 410 of the fourth module 408. The housing 410 of the second module 404 may be electrically connected to the housing 410 of the first module 402 and the housing of the third module 406. The housing 410 of the third module 406 may be electrically connected to the housing 410 of the second module 404 and the housing 410 of the fourth module 408. The housing 410 of the fourth module 408 may be electrically connected to the housing 410 of the third module 406 and the housing 410 of the first module 402. Other electrical connections between the housings 410 of the four modules 402, 404, 406, 408 may be provided.

The housings 410 of the four modules 402, 404, 406, 408 may be electrically connected in any number of ways including, for example, with wires and/or traces. In one embodiment, the electrical connections may be soldered to a first side 412 and a second side 414 near a top 416 (e.g., the ground foil 304) of each of the housings 410. The electrical connections may be soldered to the housings 410 at different locations on the housings 410.

The housings 410 are made of any number of materials with a high electrical conductivity including, for example, copper, silver, or gold. In one embodiment, one side of each of the housings 410 (e.g., the top) is thinner than the rest of the housing 410. In another embodiment, each side of the housing 410 has the same thickness.

The electrical connections between the housings 410 include an inductance in parallel with a tuning capacitor 418. The tuning capacitors 418 may be sized such that the circuit (e.g., the local coil 208) operates at a specified frequency. For example, the tuning capacitors 418 may be sized such that the local coil 208 operates at 63 MHz or 124 MHz. The tuning capacitors 418 may also be tuned such that the local coil 208 functions as a low impedance ground return at frequencies of interest to the ultrasound modules 402, 404, 406, 408 (e.g., 1-10 MHz). Each of the ultrasound modules 402, 404, 406, 408 may be low frequency coupled to ground. The low frequency coupling to ground may be provided by star grounding of the ultrasound modules 402, 404, 406, 408. Low pass filters (e.g., including capacitors 420) between the housings 410 and an ultrasound system ground provides DC pass-through. The coupling electronics (e.g., the turning capacitors 418 and the low pass filters) are designed such that the housings 410 may be effective as both a ground return at the ultrasound frequencies and an active antenna at the MR frequencies.

Within the MRI system 200, the hybrid ultrasound-MR device 400 may operate as the local coil 208 in transmit mode and/or receive mode (e.g., the hybrid ultrasound-MR device 400 may operate as a transmit RF antenna and/or a receive RF antenna). In transmit mode, RF signals generated by the processor 214, for example, may be transmitted to the hybrid ultrasound-MR device 400 via an input 422 to the first module 402. The input 422 may be soldered to a side (e.g., the first side 412) of the first module 402. Other electrical connections between the processor 214 and the hybrid ultrasound-MR device 400 may be provided (e.g., a removable electrical connection). The RF signals are conducted through the RF loop formed by the housings 210 of the four ultrasound modules 402, 404, 406, 408 and the electrical connections between the four ultrasound modules 402, 404, 406, 408. Due to the skin effect, the current density of the RF signals may be largest near the top 416 of the housings 410, for example. In one embodiment, the top 416 of the housings 410 may be etched to at least partially form the RF loop.

In receive mode, RF signals generated by the body of the patient may be received by the RF loop formed by the four ultrasound modules 402, 404, 406, 408. The received signals may be output to the receiver 212 and/or the processor 214, for example, via an output 424 of the fourth module 408. The output 424 may be soldered to a side (e.g., the second side 414) of the fourth module 408. Other electrical connections between the receiver 212 and/or the processor 214 and the hybrid ultrasound-MR device 400 may be provided (e.g., a removable electrical connection). The RF signals are conducted through the RF loop formed by the housings 210 of the four ultrasound modules 402, 404, 406, 408 and the electrical connections between the four ultrasound modules 402, 404, 406, 408. The receiver 212 and/or the processor 214 generate images based on the RF signals received from the body of the patient.

The MRI system 200 may include a number of other components upstream of the input 422 and/or downstream of the output 424. For example, the MRI system 200 may include one or more preamplifiers (e.g., a preamplifier upstream of the input 422 and a preamplifier downstream of the output 424), one or more matching capacitors, co-axial cabling, one or more baluns, one or more decoupling inductors, or a combination thereof.

The module housings 410 may be positioned in, for example, a square to form the local coil 208. The module housings 410 may be positioned relative to each other to form other shapes. For example, the hybrid ultrasound-MR device 400 may include more ultrasound modules, and the ultrasound modules may be positioned relative to one another to form a ring.

Figure 5:
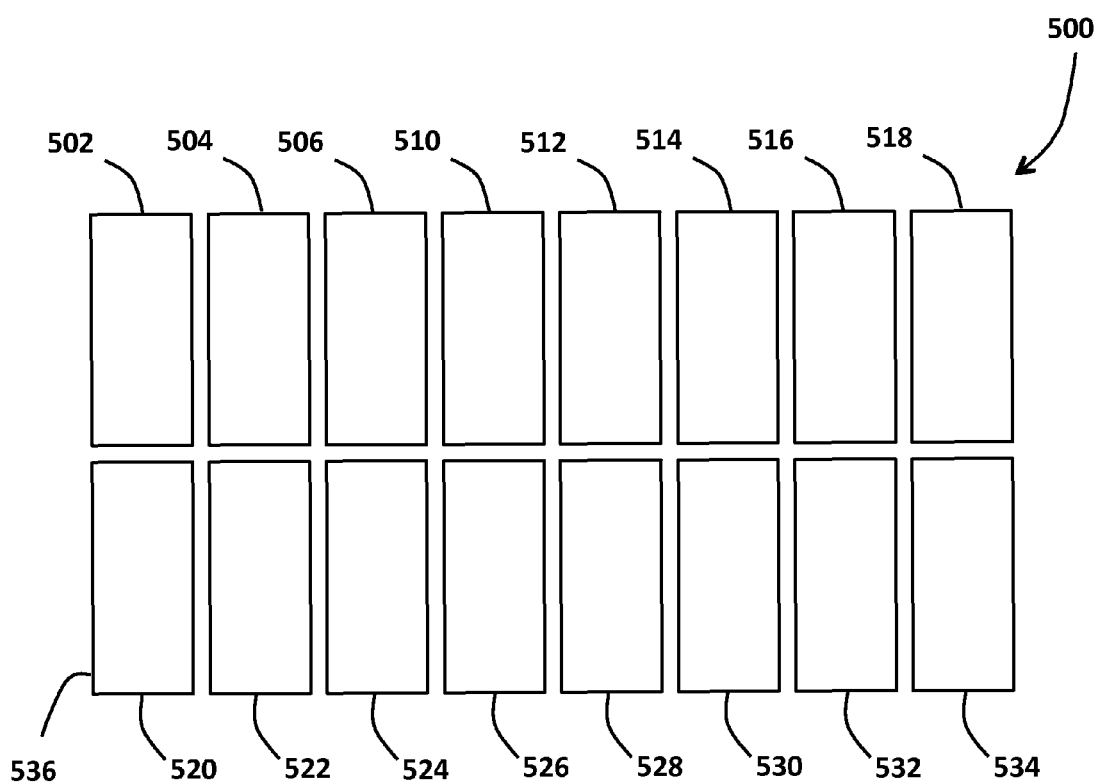
FIG. 5 shows one embodiment of a hybrid ultrasound-MR system.

FIG. 5 shows one embodiment of a hybrid ultrasound-MR system 500 that includes sixteen ultrasound modules 502, 504, 506, 508, 510, 512, 514, 516, 518, 520, 522, 524, 526, 528, 530, 532, 534 (e.g., ultrasound modules 502-534). The hybrid ultrasound-MR device 500 may include more or fewer ultrasound modules. Each of the ultrasound modules 502-534 includes a housing 536. At least some of the ultrasound modules 502-534 (e.g., housings 536) may be RF decoupled from common ground and are used to form MRI loop antennas. For example, ultrasound modules 502, 506, 520, and 524 may be connected via tuning capacitors as a first RF loop at the MRI frequency (e.g., 123 MHz). As another example, ultrasound modules 504, 510, 522, and 526 may be connected via tuning capacitors as a second RF loop at the MRI frequency. In one embodiment, all of the ultrasound modules 502-534 form a single RF loop. In another embodiment, the ultrasound modules 502-534 form four different RF loops. In yet another embodiment, less than all of the ultrasound modules 502-534 are decoupled from the common ground and used to form one or more corresponding RF loops. Other arrangements may be provided.

The RF loops formed by the ultrasound modules 502-534 may be configured such that cross-talk is minimized. For example, the RF loops may be configured such that each of the RF loops overlaps with at least one other RF loop formed by a portion of the ultrasound modules 502-534. The RF loops may be capacitively decoupled, and the RF loops may be configured such that there is zero mutual inductance between the RF loops. In some configurations of the RF loops, a ladder array, a mutually inductive array, a capacitively decoupled array, or a combination thereof may be provided.

The conflict between the ultrasound transducers and the MR coils is resolved with the MR coil occupying the same space as the ultrasound device. Both the MR coils and the ultrasound device may be operated at the same time in the same space. Compared to the solutions presented in the prior art, the MR coils may thus be operated with a high signal to noise ratio, while, also, high intensity therapeutic ultrasound (HITU) may be delivered with a high power.

Figure 6:
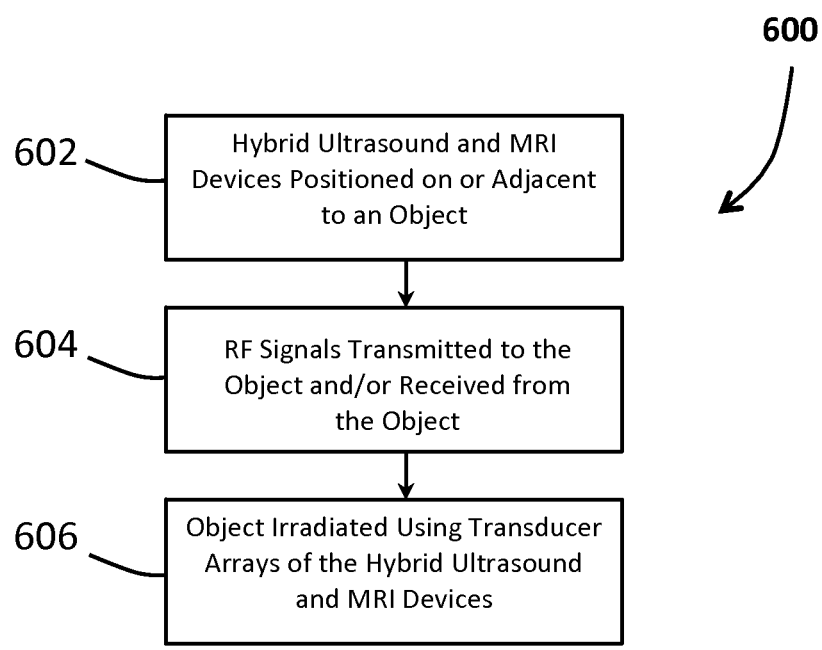
FIG. 6 shows a flowchart of one embodiment of a method for treating and imaging an object.

FIG. 6 shows a flowchart of one embodiment of a method 600 for treating and imaging an object. The method may be performed using the hybrid ultrasound-MR device 400 shown in FIG. 4 and/or the hybrid ultrasound-MR system 500 shown in FIG. 5, or another system. The method is implemented in the order shown, but other orders may be used. Additional, different, or fewer acts may be provided. Similar methods may be used for simultaneously treating and imaging an object.

In act 602, a plurality of hybrid ultrasound and MRI devices (e.g., a hybrid ultrasound and MRI system) are positioned on or adjacent to the object (e.g., a patient). Each hybrid ultrasound and MRI device of the plurality of hybrid ultrasound and MRI devices includes a transducer array and a housing operable to electromagnetically shield and enclose the transducer array. Each of the housings includes an electrically conducting side. The plurality of hybrid ultrasound and MRI devices (e.g., the housing of the plurality of ultrasound and MRI devices) are electrically connected to one another via the electrically conducting sides to form an RF loop antenna. The RF loop antenna may include four hybrid ultrasound and MRI devices. The four hybrid ultrasound and MRI devices are electrically connected to each other via tuning capacitors to form, for example, a loop (e.g., the RF loop antenna). The RF loop may include more or fewer hybrid ultrasound and MRI devices.

The hybrid ultrasound and MRI system is positioned within a bore of an MRI system. The bore is a region of the MRI system for imaging the object. The hybrid ultrasound and MRI system is positioned on a patient bed of the MRI system or on the patient. When the patient is moved into the bore for MR imaging, the hybrid ultrasound and MRI system is also moved within or is within the bore.

In act 604, RF signals are transmitted to the object, and/or signals are received from the object via the RF loop antenna. Using the MR system, a sequence of radio frequency pulses is provided to the RF loop antenna in controlled magnetic fields to generate a response from selected molecules. Additionally or alternatively, the RF loop antenna may receive the generated response from the selected molecules. Any MR sequence may be used. The response is used to generate an image. The image represents a point, line, plane, or volume (e.g., multiple planes) of the patient.

The imaging is used to locate a tumor or other region for treatment. The user and/or a processor identifies the location of the treatment region. Using a coordinate transform, the location relative to the acoustic array is determined.

In act 606, the object is irradiated using the transducer arrays of the plurality of hybrid ultrasound and MRI devices. In one embodiment, the object is irradiated using the transducer arrays while the RF signals are transmitted to the object (e.g., at the same time). Alternatively or additionally, the irradiation of the object using the transducer arrays may be performed after imaging using the RF loop antenna. Using interleaving or simultaneous treatment and imaging, the progress of treatment and/or the continued accuracy of aiming the treatment at the desired location is monitored by imaging. The transducer arrays may include HIFU transducers. In one embodiment, the transducer arrays may include ultrasound imaging transducers.

Control signals may be communicated to the hybrid ultrasound and MRI system, such as to one or more controllers in the hybrid ultrasound and MRI system. The control signals are from a user interface or other control remote from the hybrid ultrasound and MRI system. Any type of control signals may be sent, such as location, frequency, duration, aperture, amplitude, dose, pulse repetition frequency, duty cycle, or other characteristic of the ultrasound treatment. For example, steering information is sent. The mode of operation may be sent. A trigger to activate the application of therapy may be sent.

In one embodiment, the communication is optical. Light signals are sent over a fiber optic cable. Light may not interfere with the MR imaging. Alternatively, electrical signals are sent in digital or analog form.

Power is provided to drivers of the hybrid ultrasound and MRI system. The power is provided when the MRI system is turned on or configured for imaging. Alternatively, a separate power control is used. The power is cycled on and off in one embodiment. For example, the power is off whenever MR imaging is occurring. During breaks in an MRI imaging sequence, the power to the applicator is turned on and therapeutic ultrasound may be generated.

The power is provided over a cable. To avoid interference, the power may be direct current. The direct current may provide a voltage for use by pulsers to generate ultrasound waveforms. Alternatively, alternating current is provided.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A radio frequency (RF) loop antenna for a magnetic resonance imaging (MRI) system, the RF loop antenna comprising:
   housings each comprising an electrically conducting side;
   a plurality of transducer arrays, each transducer array of the plurality of transducer arrays being electromagnetically shielded and enclosed by a corresponding one of the housings and comprising a multi-dimensional array of elements;
   communications interfaces each being electromagnetically shielded and enclosed by the corresponding one of the housings, and being in communication with a corresponding transducer array of the plurality of transducer arrays; and
   tuning capacitors each electrically connecting the electrically conducting sides of two of the housings, respectively,
   wherein the electrical conducting side of the respective housing is configured to receive an RF signal from the MRI system and transmit the RF signal to the electrically conducting side of another housing of the RF loop antenna via at least one of the tuning capacitors.

2. The RF loop antenna of claim 1, further comprising resonant circuits, each of the resonant circuits being physically and electrically connected to the electrically conducting sides of two of the housings and comprising a corresponding one of the tuning capacitors.

3. The RF loop antenna of claim 1, wherein the electrically conducting sides of a subset of the housings form an RF loop, the subset of the housings electromagnetically shielding and enclosing corresponding transducer arrays of the plurality of transducer arrays, wherein the RF loop is operative at a frequency of 64 MHz or 128 MHz, and wherein each transducer array of the corresponding transducer arrays is operative at 1-5 MHz.

4. The RF loop antenna of claim 3, wherein the subset of the housings comprises four housings.

5. The RF loop antenna of claim 1, wherein the subset of housings is a first subset of the housings, wherein electrically conducting sides of the first subset of the housings form a first RF loop, and wherein the electrically conducting sides of a second subset of the housings form a second RF loop.

6. The RF loop antenna of claim 5, wherein the housings comprise a first housing, a second housing, a third housing, a fourth housing, a fifth housing, and a sixth housing, wherein the first subset comprises the first housing, the second housing, the fifth housing, and the sixth housing, and the second subset comprises the third housing and the fourth housing, and wherein the third housing is positioned between the first housing and the fifth housing, and the fourth housing is positioned between the second housing and the sixth housing.

7. The RF loop antenna of claim 1, wherein each of the housings comprises a ground foil, wherein the RF loop antenna further comprises low-pass filters, each of the low-pass filters being electrically connected between the electrically conducting side and the ground foil of the corresponding one of the housings.

8. The RF loop antenna of claim 7, wherein the first housing, the second housing, the third housing, and the fourth housing are rectangular in shape.

9. The RF loop antenna of claim 7, further comprising an ultrasound system ground, the ultrasound system ground comprising the ground foils.

10. A method for treating and imaging an object, the method comprising:
  positioning a plurality of hybrid ultrasound and magnetic resonance imaging (MRI) devices on or adjacent to the object, each hybrid ultrasound and MRI device of the plurality of hybrid ultrasound and MRI devices comprising a transducer array and a housing operable to electromagnetically shield and enclose the transducer array, each of the housings comprising an electrically conducting side, wherein the plurality of hybrid ultrasound and MRI devices are electrically connected to one another via the electrically conducting sides to form a radio frequency (RF) loop antenna and are configured to transmit received RF signals from the MRI device via the electrically connected electrically conducting sides;
  transmitting RF signals to the object or receiving signals from the object via the RF loop antenna; and
  irradiating the object using the transducer arrays of the plurality of hybrid ultrasound and MRI devices.

11. The method of claim 10, wherein irradiating the object comprises irradiating the object with ultrasound energy, wherein the method further comprises:
  receiving, at the transducer arrays, ultrasound energy reflected by the object; and
  generating an image of at least part of the object based on the reflected ultrasound energy, and wherein the object is irradiated using the transducer arrays at the same time as the RF signals are transmitted to the object, the signals are received from the object, or the RF signals are transmitted to the object and the signals are received from the object via the RF loop antenna.

12. The method of claim 10, wherein at least some of the transducer arrays are high intensity focused ultrasound (HIFU) arrays, wherein irradiating the object comprises ablating at least a portion of the object using the HIFU arrays, and wherein the portion of the object is ablated using the HIFU arrays at the same time as the RF signals are transmitted to the object, the signals are received from the object, or the RF signals are transmitted to the object and the signals are received from the object via the RF loop antenna.

\* \* \* \* \*